(12) United States Patent
Fuertes et al.

(10) Patent No.: US 7,015,318 B2
(45) Date of Patent: Mar. 21, 2006

(54) CONTINUOUS PROCESS FOR MODIFYING STARCH AND ITS DERIVATIVES BY BRANCHING ENZYMES

(75) Inventors: Patrick Fuertes, Lambersart (FR); Carole Petitjean, Marquette lez Lille (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 10/300,142

(22) Filed: Nov. 20, 2002

(65) Prior Publication Data
US 2003/0109010 A1 Jun. 12, 2003

(30) Foreign Application Priority Data
Nov. 29, 2001 (FR) .................................. 01 15433

(51) Int. Cl.
*C08B 31/00* (2006.01)
*C07H 1/00* (2006.01)
*C12P 19/18* (2006.01)

(52) U.S. Cl. ...................... 536/102; 536/124; 536/126; 435/97

(58) Field of Classification Search ................ 536/102, 536/124, 126; 435/97
See application file for complete search history.

(56) References Cited

U.S. PATENT DOCUMENTS

| 4,454,161 A | 6/1984 | Okada et al. |
| 4,957,563 A | 9/1990 | Gallaher et al. |
| 5,376,537 A | 12/1994 | Cami et al. |

FOREIGN PATENT DOCUMENTS

| EP | 0710674 | 5/1996 |
| EP | 0690170 | 9/2000 |

OTHER PUBLICATIONS

An abstract of JP-60-075295.
A Derwent abstract of WO 00/66633.

*Primary Examiner*—James O. Wilson
*Assistant Examiner*—Everett White
(74) *Attorney, Agent, or Firm*—Young & Thompson

(57) ABSTRACT

The subject of the invention is a process for modifying starch or starch derivatives by branching enzymes, consisting in continuously introducing the said branching enzymes into the reaction medium containing starch or starch derivatives.

10 Claims, No Drawings

CONTINUOUS PROCESS FOR MODIFYING STARCH AND ITS DERIVATIVES BY BRANCHING ENZYMES

The present invention relates to a process for modifying starch and its derivatives by branching enzymes.

More particularly, the invention relates to a process for modifying starch and starch derivatives in which the branching enzymes are continuously introduced into the reaction medium.

Starch consists of two polymers, amylose and amylopectin. Amylose is the fraction containing linear α-1,4 linked glucose homopolymers and a few α-1,6 branching points. Amylopectin is, for its part, the branched fraction consisting of linear α-1,4 glucose chains linked to other linear α-1,4 glucose chains by α-1,6 branching points.

The combination of these two homopolymers, packed in the form of very well structured starch granules, constitutes the carbon source reserve for the plant.

The starch produced in each plant consists of a variable percentage of each of its amylose and amylopectin constituents, or even of a particular molecular weight distribution of each of the said glucose homopolymers. That explains the reason why the various starches and their derivatives are usually classified according to their botanical origin.

The functional properties of starches and of their derivatives are in addition directly dependent on their amylose and amylopectin content.

Thus, when a starch suspension is heated above the gelatinization temperature, the starch granule swells, and the amylose becomes preferentially solubilized.

However, during the cooling of this paste, in particular under particular temperature and dry matter conditions, the glucose homopolymers retrograde, rapidly for amylose (a few hours), and more slowly for amylopectin (a few days).

The expression retrogradation is understood to mean the tendency which amylose and amylopectin macromolecules have, during the cooling of the said paste, to recombine with each other by forming hydrogen bonds.

In practice, it results in an opacification and an increase in viscosity during the cooling of the paste and in the formation, in the cold state, of a three-dimensional gel structure.

Specialists in the field of the use of starches and of starch derivatives in the food industry are unanimous in saying that this retrogradation phenomenon affects more particularly the texture of foods, and decreases the shelf life thereof.

Furthermore, the solubilization of amylose during the cooking of starch, followed by cooling, promotes its complexing with the residual lipids of the starch.

Amylose indeed exists in a helical form into which the lipids may become inserted, thus generating amylose-lipid complexes.

These amylose-lipid complexes also lead to the formation of insolubles which disrupt the Theological behaviour especially of the pastes prepared from these starches and thus impair their colloidal state.

This will result in the paper industry in numerous technological problems both in the blocking of filters and in the quality of the paper.

It is known to make these products more acceptable by preparing them from amylopectin-rich starchy substances, and therefore for example from waxy varieties.

A limitation in the formation of amylose-lipid complexes also quite obviously results therefrom.

However, the stability of the gels and binding agents obtained from the said amylopectin-rich starchy products is not sufficient for the requirements of food industries where it is sometimes necessary to have a period of storage of several months.

A first solution consists in stabilizing the glucose homopolymers, this being by means of chemical agents. This operation is most often carried out using esterification and etherification reactions. It may involve in particular acetylation and hydroxypropylation reactions. In addition, to obtain the desired textural and viscosity properties, these reactions are often combined with a crosslinking reaction.

These modifications then confer remarkable theological properties on the starches, making them more resistant to mechanical treatments such as shearing, or to acid media. Acetylation or hydroxypropylation additionally confer good stability during storage after cooking, in particular at low temperature.

However, the products thus obtained have the disadvantage of having been chemically treated, which is often poorly perceived by consumers.

An alternative to the processes aimed at chemically modifying the native starches of mutant, hybrid or genetically modified plants consists in introducing in vitro new branching points into the starch.

This then involves arriving at a rearrangement of the amylopectin or amylose chains rather than using stabilizing and/or crosslinking reactions as indicated above.

One technique consists in using purified enzymes for the biosynthesis of glycogen and/or starch, such as glycogen or starch branching enzymes, which are respectively responsible for the synthesis of the α-1,6 branching points in glycogen, or of the α-1,6 branching points in amylopectin and of the few branching points in amylose.

A process is thus described in JP 60-752,95 for the production of water-soluble starchy substances and for the manufacture of foods or drinks containing them, consisting in collecting the water-soluble fraction of the product derived from the action of a branching enzyme on a gelatinized starchy substance.

The reaction is then carried out batchwise, i.e. by mixing, with no special precaution, the starchy substance to be modified and the branching enzyme.

Likewise in patent FR 2,499,588 which covers a branching enzyme and the production of improved foods, a solution of starchy substances, which is prepared by gelatinization and dispersion, is first subjected to the action of the branching enzyme, and is then mixed with no subsequent treatment or, if necessary, after concentration and/or drying, with the food products.

The starchy substance is also heated in the presence of the branching enzyme in order to simultaneously carry out the gelatinization and the enzymatic reaction, and the resulting product is then incorporated into the food products as desired.

However, the branching enzymes used in the said patent have relatively low optimum temperatures for action (of the order of 30° C. for the enzyme extracted from *E. coli* or from potato, and of the order of 25° C. for *Bacillus megaterium*).

It is known in most cases that the gelatinization temperature of a starchy substance is less than 100° C., but industrial cooking, which involves high dry matter contents and a short cooking time, conventionally requires temperatures greater than 100° C. (between 110 and 170° C.), temperatures which are quite obviously incompatible with those for optimum functioning of the enzymes used.

The practice recommended in patents JP 60-752,95 and FR 2,499,588 is to gelatinize the starchy substances under temperature conditions which are achieved at the detriment of optimum activity of the branching enzymes used.

This manner of proceeding therefore does not make it possible to reconcile the Theological behaviour of the starchy substance to be treated with the mode of action of the branching enzymes.

The teaching of patent EP 690,170 relating to a process for couching and surfacing paper is part of this same rationale, because it is considered that the gelatinization of starch is the essential factor, it being necessary for the starch to be absolutely gelatinized in order to allow effective action of the branching enzymes.

It is thus described to gelatinize starch batchwise or continuously, while the enzyme is introduced in an undifferentiated way, either before or after the said gelatinization.

A partial solution has been offered to this difficulty of reconciling optimization of the enzymatic reaction with gelatinization conditions in patent application EP 710,674, where the use of the potato branching enzyme, or the use of a branching enzyme derived from a heat-resistant organism, is described.

In the first case, it is recommended to use a branching enzyme isolated from potato because its production in a large quantity presents no major difficulty. The excess enzyme supplied to the reaction medium therefore compensates for the high loss of enzymatic activity which is unsatisfactory.

This solution is hardly satisfactory because in no case does it make it possible to control the enzymatic reaction.

In the second case, the enzyme is recommended because it has a higher temperature optimum than that of the potato branching enzyme.

However, the increase in heat tolerance of the enzymes does not automatically mean a better quality of the products generated.

The use of these enzymes solves the problem of heat shock during the introduction of the enzyme into the reaction medium.

However, the appearance of amylose-lipid complex type structures in the pastes obtained after modification of the starch by the said heat-resistant branching enzymes has been observed by the applicant company.

It results from the preceding text that there is therefore an unsatisfied need for having available an effective process for modifying starch or starch derivatives with branching enzymes.

This process requires in particular that operating conditions are established which make it possible to direct, on the one hand, the temperatures required for industrial cooking of starches and of starch derivatives, and, on the other hand, the temperatures corresponding to the optimum activity of the branching enzymes.

These operating conditions should then make it possible to optimize the operation of the branching enzymes by limiting the formation, in the reaction medium, of insoluble substances, it being possible for the latter to be in particular particles resulting from the retrogradation of starch or of the complexes derived from the structured combination with lipids, these insoluble substances hindering the accessibility of the enzymes to the branching sites of the carbohydrate chains, and being capable of leading to the impairment of the quality of the products formed.

Without being bound by any theory, the expression "structured amylose-lipid combinations" is understood by the applicant company to mean a possible crystalline type organization of the amylose and of the lipids.

The applicant company had the merit of reconciling all these objectives which were until now reputed to be difficult to reconcile by designing and producing, at the cost of numerous research studies, a process for modifying starch or starch derivatives by branching enzymes which consists in continuously introducing the said branching enzymes into the reaction medium containing starch or starch derivatives.

The process for modifying starch or starch derivatives by branching enzymes in accordance with the invention consists in a first instance in heating the starch or starch derivatives so as to be in partially or completely gelatinized form.

This first stage of the process in accordance with the invention ensures the solubilization of the starch, or of a starch derivative, which is capable of being treated with the branching enzymes.

The expression "starch" is understood to mean, for the purposes of the invention, a starch chosen from the group consisting of maize, potato, wheat, pea, cassava and rice starches.

The expression "starch derivatives" is understood to mean the products of acid or enzymatic hydrolysis of starch, and also the products of the chemical and physical modifications of starch of any type.

In one embodiment of the process in accordance with the invention, a starch milk having a dry matter content of between 5 and 50% is prepared, which is heated, by any technique otherwise known to persons skilled in the art, to a temperature which is equal to or greater than the gelatinization temperature of starch, preferably between at least 100 and at most 200° C., still more preferably between at least 110 and at most 170° C.

The expression "branching enzymes" is understood to mean, for the purposes of the invention, the branching enzymes chosen from the group consisting of glycogen branching enzymes, starch branching enzymes, cyclomaltodextrin glucosyl transferases, transglucosidases and any mixtures of these enzymes.

More particularly, these branching enzymes are extracted from organisms and/or microorganisms chosen from the group consisting of higher plants, yeasts, bacteria and unicellular algae.

After this step of total or partial solubilization of the starch milk or of the starch derivative milk, branching enzymes are continuously introduced, in accordance with the invention, into the reaction medium under conditions which limit the formation of intermolecular complexes.

More particularly, the conditions for introducing the branching enzymes into the reaction medium are set with respect to time and the temperatures so as to limit the formation of the insolubles derived from the retrogradation of starch and of the structured amylose-lipid combinations.

The starch milk thus partially or completely gelatinized is therefore cooled, in accordance with the invention, so as to bring it to the temperature optimum for the branching enzyme chosen.

The applicant company has found that it is necessary here to cool continuously, rapidly and in a controlled manner the partially or completely gelatinized starch milk until the temperature for optimum operation of the branching enzyme is obtained.

For example, if the glycogen branching enzyme extracted from *Escherichia coli* or from microorganisms of the genus *Bacillus* (*B. stearothermophilus*, *B. megaterium*.), or produced from a genetically modified organism, is chosen, the starch paste should be brought to the temperature for optimum operation of the enzyme, i.e. between 20 and 30° C., or between 60 and 75° C., if the enzyme is derived from a heat-resistant microorganism such as *B. stearothermophilus*.

It will be advantageously chosen to rapidly cool the solution of starch or of partially or completely gelatinized starch derivatives from its initial temperature of between 100 and 200° C., under conditions such that they make it possible to avoid the retrogradation of the starch or the formation of structured amylose-lipid combinations, e.g. between 1 and 15 min, as will be exemplified below.

The pH of the solution is then adjusted so as to bring it to a value consistent with the mode of operation of the said enzyme.

Another essential characteristic of the invention consists in this step of continuously introducing the branching enzymes.

The applicant company has thus had the merit of showing that it is in fact by continuously adding the branching enzymes to the reaction medium that it is possible to optimize the degree of modification of the starches or starch derivatives thus treated, and not by adjusting the gelatinization conditions, as it was recommended to do in the state of the art.

For example, with the purified *E. coli* glycogen branching enzyme, it is advantageously chosen to continuously add enzyme diluted between 0.5 and 15 mg/ml of proteins at a rate of between 90 and 600 ml/h to a stream of the solution of starch or of starch derivatives, from 5 to 50% dry matter content at a rate of between 0.5 and 50 l/h and cooled between 30 seconds and 15 minutes, as will be exemplified below.

At the end of the reaction, the enzyme will be finally heat-deactivated. In the case of an enzyme having a temperature optimum of 30° C., it is accepted that an increase in temperature of 70° C. over an appropriate period completely inactivates the said enzyme. For a branching enzyme having a temperature optimum at 70° C., the heat-inactivation will be carried out at 100° C.

The efficacy of the process in accordance with the invention compared with conventional processes for modifying starches and starch derivatives is determined by monitoring the following analytical parameters.

The determination of the level of $\alpha$-1,6 bonds, resulting from the action of the branching enzyme, that of the molar mass of the products thus modified and the reducing sugar content are carried out as indicated in patent application WO 00/66633 of which the applicant company is the proprietor.

The measurement of the viscosity of the solution of starch or of starch derivatives thus treated is carried out according to the following test. The analysis of viscosity consists, according to the products to be analysed, in weighing a mass of dry product (3 g dry for a standard or chemically modified maize starch, 4.5 g dry for a waxy maize starch), in adding thereto 6.75 g of glycerol at 98% purity in the bowl of a "Rapid Visco Analyzer" (RVA Newport), and then in adjusting to 28 g with demineralized water.

It is also possible to measure the viscosity of a mass of dry product in the absence of glycerol, in this case 7 g dry matter for a standard maize starch adjusted to 28 g with demineralized water.

The whole is then carefully homogenized. The time/temperature and RVA rate profile is then established as follows. The sample is stirred at 100 rpm at a temperature of 25° C. for 5 s, and then at 500 rpm for 15 S.

The stirring is maintained at 160 rpm for the remainder of the profile. The initial temperature of 25° C. is maintained for 10 min, and then it is increased to 90° C. over 8 min. This temperature is maintained for 3 min, and then reduced to 30° C. over 8 min and maintained at this value of 30° C. for 5 min.

The viscosity selected is the viscosity measured in centipoises at the end of the profile at 30° C., at 34 min. The RVA bowls are then stored at 4° C. for 7 d and then another record of the viscosity is made. For that, the sample is stirred at 160 rpm at 30° C. for 20 min. The viscosity selected is the mean of the viscosity between 15 and 20 min.

Other characteristics and advantages of the invention will emerge on reading the nonlimiting examples described below.

EXAMPLE 1

Two tests are carried out batchwise and continuously on standard maize starch with purified glycogen branching enzyme derived from *E. coli* as indicated below.

For the "batch" modifying process, a starch milk containing 10% dry matter content is prepared. The solubilization is carried out by passing through a tubular cooker heated by a thermal fluid at 145° C. under a pressure of 4 to 5 bar, at a rate of 40 ml/min.

1 kg of paste is recovered at a temperature of close to 100° C. and then cooled over 2 hours, with stirring, to a temperature of 30° C.

The pH is adjusted to a value of the order of 7.5 with 0.1 N NaOH. 0.84 mg of enzyme purified to homogeneity per gram of starch is directly introduced into the solution at 30° C. and the reaction is carried out for 20 h 45 min. At the end of the reaction, the enzyme is deactivated by heating to 70° C.

For the continuous process, the same starch milk containing 10% dry matter content is solubilized by passing through a tubular cooker heated by a thermal fluid at 145° C. under a pressure of 4 to 5 bar, at a rate of 18 ml/min.

The cooling is carried out at this same rate over 5 minutes by passing into two coolers at −5° C. in order to reach 30° C.

The pH is continuously adjusted to 7.5 with 0.1 N NaOH, and the enzyme diluted to 1.2 mg/ml is continuously introduced at a rate of 1.6 ml/min before an on-line mixer.

The reaction is carried out in a thermostated reactor at 30° C. for 20 h 45 min, and at the end of the reaction, the enzyme is deactivated by heating to 70° C.

Table I gives the values of the levels of branching, of the molar mass, of the viscosity and the reducing sugar content of the batch (B) and continuously (C) modified standard starches compared with the control (A).

For the control (A), a standard maize starch milk containing 10% DM is prepared. The solubilization is carried out by passing into a tubular cooker heated by a thermal fluid at 145° C. under a pressure of 4 to 5 bar at a rate of 40 ml/min. The solution is then cooled to 30° C.

TABLE I

|   | Reducing sugars (%) | Level of $\alpha$-1,6 bonds | Molar mass MW (Daltons) | RVA viscosity (cPoises) Initial | 7 d |
|---|---|---|---|---|---|
| A | 0.15 | 3.4 | $5 \times 10^6$ | 16,100 | gel |
| B | 0.16 | 3.5 | $4.6 \times 10^6$ | 54 | 47 |
| C | 0.16 | 5.6 | $2.9 \times 10^6$ | 23 | 26 |

For products B and C, the same stability of the solutions is observed and the same reducing sugar content is observed (which indeed confirms the redistribution of the chains without hydrolysis of the starch treated and the absence of contaminating amylase activities) compared with the control.

On the other hand, by virtue of the continuous process, the branching level is significantly increased, and the molar mass lower, with a very low dispersion of the masses.

The chromatographic analyses of the molecular weight distribution profiles indeed clearly show the difference between the products B and C.

The distribution is very narrow and centred over $2 \times 10^5$ Daltons for product C, whereas it is more spread out, "polydisperse" and centred over $3 \times 10^5$ Daltons for product B.

It is also observed that the viscosity of product C in solution is lower than that of product B.

The continuous process in accordance with the invention therefore indeed makes it possible to optimize the enzymatic reaction.

Indeed, this example clearly shows that the reactivity of the branching enzyme is better during the continuous process, the latter making it possible in particular to greatly limit retrogradation of the starch.

EXAMPLE 2

Two tests are carried out batchwise and continuously on standard maize starch with purified glycogen branching enzyme derived from *E. coli* as indicated in Example 1, the only difference being that the enzymatic reaction is carried out at 60° C.

This reaction temperature is much higher than the reaction optimum temperature for the enzyme isolated from *E. coli*, but it has the advantage of being more consistent with the conventional industrial conditions for using industrial enzymes.

It was therefore important to test the efficiency of the process in accordance with the invention under such operating conditions.

For the "batch" modifying process, a starch milk containing 10% dry matter content is prepared.

The solubilization is carried out by passing through a tubular cooker heated by a thermal fluid at 145° C. under a pressure of 4 to 5 bar, at a rate of 27 ml/min.

0.5 kg of paste is recovered at a temperature of close to 100° C. and then cooled over 2 h 30 min, with stirring, in order to obtain the temperature of 60° C.

The pH is adjusted to around 7.5 with 0.1 N NaOH and 2.2 mg of enzyme purified to homogeneity per gram of starch are directly introduced into the solution at 60° C. and the reaction is carried out for 19 h. At the end of the reaction, the enzyme is deactivated by heating to 70° C.

For the continuous process, the same starch milk containing 10% dry matter content is solubilized by passing through a tubular cooker heated by a thermal fluid at 145° C. under a pressure of 4 to 5 bar, at a rate of 35 ml/min.

The cooling is carried out at this same rate over 6 minutes in order to reach 60° C. The pH is continuously adjusted to 7.5 with 0.1 N NaOH, and the enzyme diluted to 3.1 mg/ml is continuously introduced at a rate of 2.5 ml/min before an on-line mixer.

The reaction is carried out in a thermostated reactor at 60° C. for 22 h 30 min and, at the end of the reaction, the enzyme is deactivated by heating to 70° C.

Table II gives the values of the branching levels, of the molar mass, of the viscosity and the reducing sugar content of the standard starches modified batchwise (E) and continuously (F) compared with the control (D).

For the control (D), a standard maize starch milk containing 10% DM is prepared. The solubilization is carried out by passing through a tubular cooker heated by a thermal fluid at 145° C. under a pressure of 4 to 5 bar, at a rate of 28 ml/min. The solution is then cooled to 60° C.

TABLE II

| | Reducing sugars (%) | Level of α-1,6 bonds | Molar mass MW (Daltons) | RVA viscosity (cPoises) Initial | 7 d |
|---|---|---|---|---|---|
| D | 0.1 | 3.4 | $>5 \times 10^6$ | 17,003 | gel |
| E | 0.1 | 3.2 | $>5 \times 10^6$ | 11,953 | gel |
| F | 0.1 | 3.8 | $>5 \times 10^6$ | 3675 | gel |

The continuous addition of the enzyme, even at a temperature which is barely tolerated by the branching enzyme, makes it possible to improve the branching level of the starch thus obtained, and to confer new physicochemical properties on it, as the results of viscosity of the solution which are obtained in fact illustrate.

This example also illustrates the advantage of the process with continuous addition of the enzyme.

Indeed, even at a temperature which limits the phenomena of retrogradation of standard maize starch, the continuous addition of the branching enzyme makes it possible to obtain a product whose characteristics are improved compared with the product produced with a batch process.

EXAMPLE 3

A test is carried out with a waxy maize, although it is understood that a starch of this quality has a weaker tendency towards retrogradation.

However, it is also accepted that in particular in the paper industry applications, for example after an oxidizing treatment, it is difficult to maintain the stability of the preparations prepared from the said waxy starch.

It was therefore of interest to try to obtain, after continuous modification, a waxy starch which is even more processed than during a batch modification process.

For the "batch" modifying process, a waxy starch milk containing 15% dry matter content is prepared.

The solubilization is carried out by passing through a tubular cooker heated by a thermal fluid at 145° C. under a pressure of 4 to 5 bar, at a rate of 25 ml/min.

1 kg of paste is recovered at a temperature of close to 100° C. and then cooled over 4 h 15 min, with stirring, in order to obtain the temperature of 30° C.

The pH is adjusted to around 7.5 with 0.1 N NaOH and 2.1 mg of enzyme purified to homogeneity per gram of starch are directly introduced into the solution at 30° C. and the reaction is carried out for 20 h. At the end of the reaction, the enzyme is deactivated by heating to 70° C.

For the continuous process, the same starch milk containing 15% dry matter content is solubilized by passing through a tubular cooker heated by a thermal fluid at 145° C. under a pressure of 4 to 5 bar, at a rate of 25 ml/min.

The cooling is carried out at this same rate over 5 to 10 minutes in order to reach 30° C. The pH is continuously adjusted to 7.5 with 0.1 N NaOH, and the enzyme diluted to 3.1 mg/ml is continuously introduced at a rate of 2.5 ml/min before an on-line mixer.

The reaction is carried out in a thermostated reactor at 30° C. for 22 h 30 min and, at the end of the reaction, the enzyme is deactivated by heating to 70° C.

Table III gives the values of the branching levels, of the molar mass, of the viscosity and the reducing sugar content of the standard starches modified batchwise (H) and continuously (I) compared with the control (G).

For the control (G), a waxy maize starch milk containing 15% DM is prepared. The solubilization is carried out by passing through a tubular cooker heated by a thermal fluid at 145° C. under a pressure of 4 to 5 bar, at a rate of 25 ml/min. The solution is then cooled to 30° C.

TABLE III

|   | Reducing sugars | Level of α-1,6 bonds | Molar mass MW | RVA viscosity (cPoises) | |
|---|---|---|---|---|---|
|   | (%) |   | (Daltons) | Initial | 7 d |
| G | 0.03 | 4.3 | >5 × 10⁶ | 4120 | 8096 |
| H | 0.04 | 6.5 | 2.8 × 10⁵ | 50 | 60 |
| I | 0.05 | 7.8 | 2.5 × 10⁵ | 54 | 65 |

The continuous treatment according to the invention of waxy starch with the branching enzyme therefore makes it possible, compared with the batch process, to significantly increase the branching level and to generate products still having good stability over time and a satisfactory Theological behaviour.

EXAMPLE 4

A test is carried out with a waxy maize, as in Example 3, but a treatment is carried out with the branching enzyme at 60° C.

For the "batch" modifying process, a waxy starch milk containing 15% dry matter content is prepared.

The solubilization is carried out by passing through a tubular cooker heated by a thermal fluid at 145° C. under a pressure of 4 to 5 bar, at a rate of 22 ml/min.

0.5 kg of paste is recovered at a temperature of close to 100° C. and then cooled over 1 h 30 min, with stirring, in order to obtain the temperature of 60° C.

The pH is adjusted to around 7.5 with 0.1 N NaOH and 2.2 mg of enzyme purified to homogeneity per gram of starch are directly introduced into the solution at 60° C. and the reaction is carried out for 19 h. At the end of the reaction, the enzyme is deactivated by heating to 70° C.

For the continuous process, the same starch milk containing 15% of dry matter content is solubilized by passing through a tubular cooker heated by a thermal fluid at 145° C. under a pressure of 4 to 5 bar, at a rate of 25 ml/min.

The cooling is carried out at this same rate over 8 minutes in order to reach 60° C. The pH is continuously adjusted to 7.5 with 0.1 N NaOH, and the enzyme diluted to 3.1 mg/ml is continuously introduced at a rate of 2.9 ml/min before an on-line mixer.

The reaction is carried out in a thermostated reactor at 60° C. for 22 h 30 min and, at the end of the reaction, the enzyme is deactivated by heating to 70° C.

Table IV gives the values of the branching levels, of the molar mass, of the viscosity and the reducing sugar content of the waxy starches modified batchwise (K) and continuously (L) compared with the control (J).

For the control (J), a waxy maize starch milk containing 15% DM is prepared. The solubilization is carried out by passing through a tubular cooker heated by a thermal fluid at 145° C. under a pressure of 4 to 5 bar, at a rate of 22 ml/min. The solution is then cooled to 60° C.

TABLE IV

|   | Reducing sugars | Level of α-1,6 bonds | Molar mass MW | RVA viscosity (cPoises) | |
|---|---|---|---|---|---|
|   | (%) |   | (Daltons) | Initial | 7 d |
| J | 0.03 | 4.7 | 5 × 10⁶ | 2589 | 6511 |
| K | 0.03 | 4.8 | >5 × 10⁶ | 2303 | gel |
| L | 0.04 | 6.3 | >5 × 10⁶ | 2105 | 3382 |

The continuous treatment according to the invention of waxy starch with the branching enzyme therefore makes it possible, compared with the batch process, to significantly increase the branching level and to generate products still having good stability over time and a rheological behaviour which is completely consistent with the modifications carried out batchwise.

EXAMPLE 5

Two tests are carried out batchwise and continuously on standard maize starch with purified glycogen branching enzyme derived from *B. stearothermophilus* as indicated below.

For the "batch" modifying process, a starch milk containing 10% dry matter content is prepared.

The solubilization is carried out by passing through a tubular cooker heated by a thermal fluid at 145° C. under a pressure of 4 to 5 bar, at a rate of 32 ml/min.

1.8 kg of paste are recovered at a temperature of close to 100° C. and then cooled over 1 h 30 min, with stirring, in order to obtain the temperature of 70° C.

The pH is adjusted to around 6.5 with 0.1 N NaOH and 0.026 mg of enzyme purified to homogeneity per gram of starch are directly introduced into the solution at 70° C. and the reaction is carried out for 23 h. At the end of the reaction, the enzyme is deactivated by heating to 100° C.

For the continuous process, the same starch milk containing 10% dry matter content is solubilized by passing through a tubular cooker heated by a thermal fluid at 145° C. under a pressure of 4 to 5 bar, at a rate of 32 ml/min.

The cooling is carried out at this same rate over 5–10 minutes in order to reach 70° C. The pH is continuously adjusted to 6.5 with 0.1 N NaOH, and the enzyme diluted to 0.026 mg/ml is continuously introduced at a rate of 3.3 ml/min before an on-line mixer.

The reaction is carried out in a thermostated reactor at 70° C. for 23 h and, at the end of the reaction, the enzyme is deactivated by heating to 100° C.

Table V gives the values of the branching levels, of the molar mass, of the viscosity and the reducing sugar content of the standard starches modified batchwise (N) and continuously (O) compared with the control (M).

For the control (M), a standard maize starch milk containing 10% DM is prepared. The solubilization is carried out by passing through a tubular cooker heated by a thermal fluid at 145° under a pressure of 4 to 5 bar, at a rate of 32 ml/min. The solution is then cooled to 70° C.

TABLE V

|   | Reducing sugars (%) | Level of α-1,6 bonds | Molar mass MW (Daltons) | RVA viscosity (cPoises) Initial | RVA viscosity (cPoises) 7 d |
|---|---|---|---|---|---|
| M | 0.1 | 3.4 | >5 × 10$^6$ | >24,000 | gel |
| N | 0.13 | 6.8 | 1.6 × 10$^5$ | 153 | 150 |
| O | 0.12 | 6.5 | 1.8 × 10$^5$ | 99 | 106 |

The results apparently show no significant differences between the batch treatment and the continuous treatment of standard maize starch with the heat-resistant branching enzyme derived from *B. stearothermophilus*.

However, the pastes thus obtained, which are collected after deactivation of the enzyme at 100° C. and centrifuged, have precipitates which are completely different in quantities between the batch treatment and the continuous treatment.

These precipitates correspond to structures such as those obtained by complexing the lipids with the amylose fraction of the treated starch.

In the batch process for modifying starch, these precipitates reach the order of 12.9% by weight of the paste, whereas the continuous treatment makes it possible to limit these precipitates by a factor of the order of 4.

The continuous starch modifying process in accordance with the invention is therefore particularly well suited to the preparation of pastes of excellent quality.

The invention claimed is:

1. A method of modifying starch or starch derivatives by branching enzymes while limiting formation of intermolecular complexes, the branching enzymes being extracted from organisms or microorganisms selected from the group consisting of higher plants, yeasts, bacteria and unicellular algae, wherein the following steps are successively performed:
the starch or starch derivatives are heated so as to be in partially or completely gelatinized form, thus forming a reaction medium,
the reaction medium is cooled within 1 to 15 minutes until the temperature for optimum operation of the branching enzyme is obtained,
the branching enzymes are continuously introduced into the reaction medium under conditions which limit the formation of intermolecular complexes;
wherein the continuous introduction of the branching enzymes into the reaction medium is carried out under conditions which limit the retrogradation of starch or of starch derivatives and the formation of structured amylose-lipids.

2. The method as claimed in claim 1, wherein the conditions for continuously introducing the branching enzymes into the reaction medium are set with respect to the time and the temperatures.

3. The method as claimed in claim 1, wherein the temperature of the reaction medium during the introduction of the branching enzymes is between 20 and 75° C.

4. The method as claimed in claim 1, wherein branching enzymes are selected from the group consisting of glycogen branching enzymes, starch branching enzymes, cyclomaltodextrin glucosyl transferases, transglucosidases and any mixtures of these enzymes.

5. The method as claimed in claim 1, wherein the starch is selected from the group consisting of maize, potato, wheat, pea, cassava and rice starches.

6. The method as claimed in claim 1, wherein the starch derivatives are selected from the group consisting of the products of acid or enzymatic hydrolysis of starch, and also the products of the chemical and physical modifications of starch of any type.

7. The method according to claim 1, wherein the reaction medium is cooled within 5–15 minutes.

8. The method as claimed in claim 7, wherein branching enzymes are selected from the group consisting of glycogen branching enzymes, starch branching enzymes, cyclomaltodextrin glucosyl transferases, transglucosidases and any mixtures of these enzymes.

9. The method as claimed in claim 7, wherein the starch is selected from the group consisting of maize, potato, wheat, pea, cassava and rice starches.

10. The method as claimed in claim 7, wherein the temperature of the reaction medium during the introduction of the branching enzymes is between 20 and 75° C.

* * * * *